United States Patent [19]

Wittry

[11] Patent Number: 4,882,780
[45] Date of Patent: Nov. 21, 1989

[54] SCANNING MONOCHROMATOR CRYSTAL AND RELATED METHOD

[75] Inventor: David B. Wittry, Pasadena, Calif.

[73] Assignee: University of Southern California, Los Angeles, Calif.

[21] Appl. No.: 309,304

[22] Filed: Jan. 3, 1989

Related U.S. Application Data

[60] Division of Ser. No. 833,450, Feb. 26, 1986, Pat. No. 4,807,268, which is a continuation-in-part of Ser. No. 549,366, Nov. 4, 1983, Pat. No. 4,599,741.

[51] Int. Cl.$^4$ ................................................ C21K 1/06
[52] U.S. Cl. .......................................... 378/84; 378/85
[58] Field of Search ..................................... 378/82–85, 378/45, 49, 81

[56] References Cited

U.S. PATENT DOCUMENTS

| | | | |
|---|---|---|---|
| 3,546,453 | 12/1970 | Browning . | |
| 3,914,605 | 10/1975 | Hara . | |
| 4,446,568 | 5/1984 | Williams | 378/84 |
| 4,599,741 | 7/1986 | Wittry | 378/82 |
| 4,649,557 | 3/1987 | Hornstra et al. | 378/84 |
| 4,807,268 | 2/1989 | Wittry | 378/84 |

OTHER PUBLICATIONS

R. W. James, "The Optical Principles of the Diffraction of X-Rays", *The Crystalline State*, Vol. II, pp. 268–305 (1958).

*Primary Examiner*—Carolyn E. Fields
*Assistant Examiner*—David P. Porter
*Attorney, Agent, or Firm*—Nilsson, Robbins, Dalgarn, Berliner, Carson & Wurst

[57] ABSTRACT

A doubly-curved crystal for use in a scanning monochromator is oriented with respect to a reference plane containing source and image locations of the monochromator. The crystal has concave planes of lattice points and a concave crystal surface which satisfy Johannson geometric conditions within the reference plane for a Rowland circle of radius R. The planes of lattice points are substantially spherically curved to a radius of 2R, and the crystal surface is substantially toroidally curved with a radius of substantially 2R within a plane perpendicular to the reference plane. The crystal may be formed by plastically deforming a cylindrically curved crystal blank over a doubly-curved convex die.

10 Claims, 8 Drawing Sheets

FIG. 2
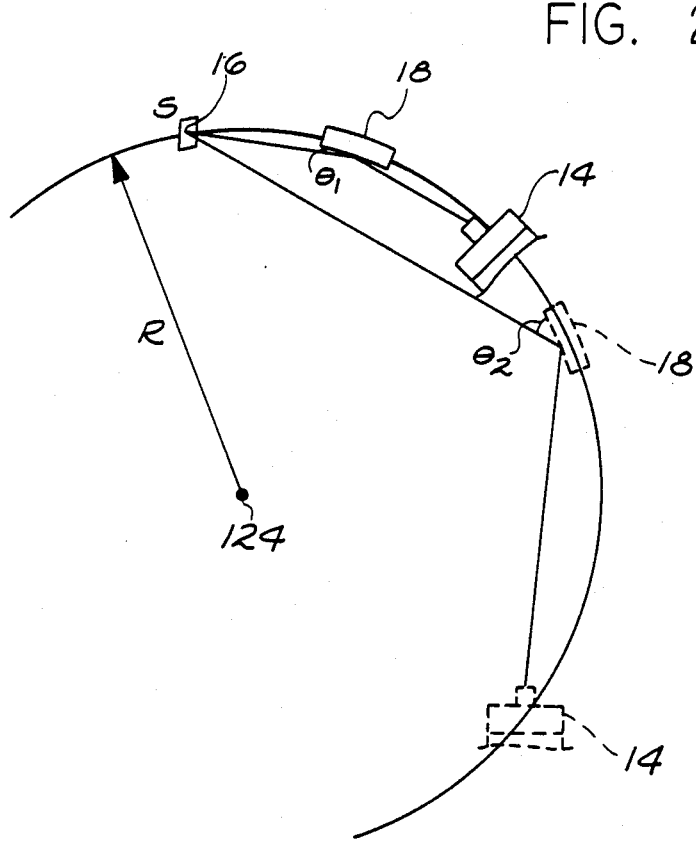
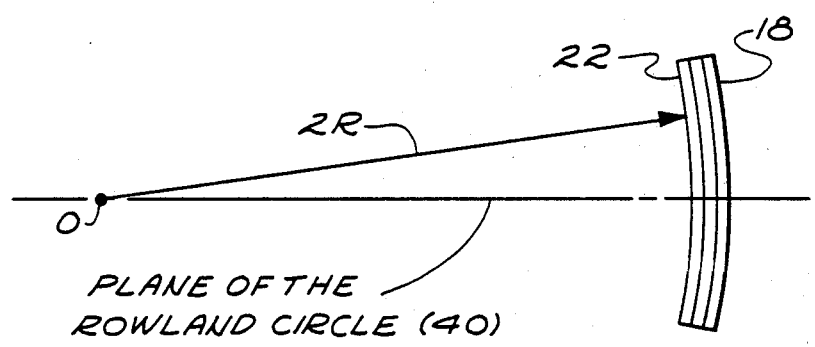
PLANE OF THE
ROWLAND CIRCLE (40)
FIG. 3B

FIG. 5A
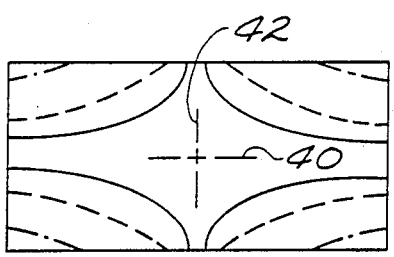
$\theta_B = 15$
FIG. 5B
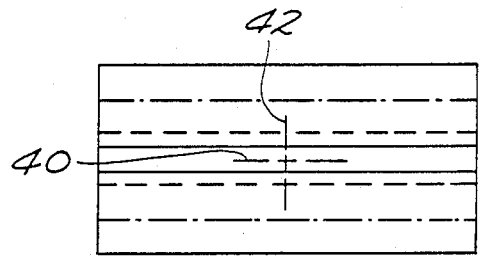
$\theta_B = 15, 75$
FIG. 5C
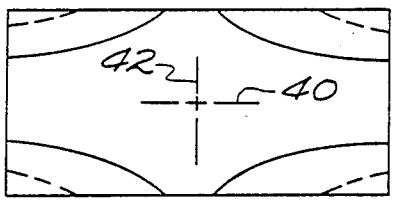
$\theta_B = 30$
FIG. 5D
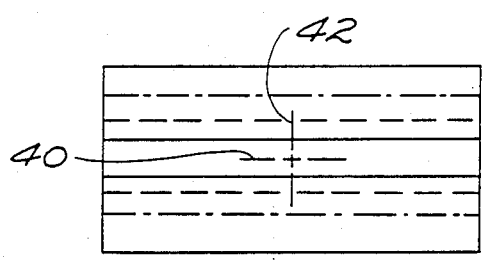
$\theta_B = 30, 60$
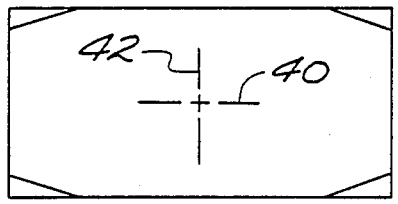
$\theta_B = 45$
FIG. 5E
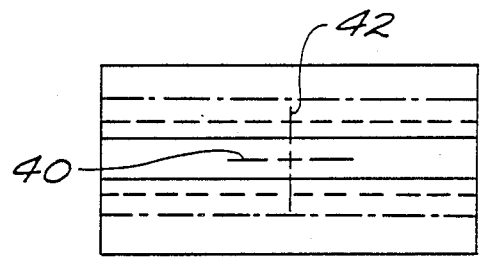
$\theta_B = 45$
FIG. 5F

SCANNING MONOCHROMATOR CRYSTAL AND RELATED METHOD

BACKGROUND OF THE INVENTION

This is a divisional application of application Ser. No. 833,950, now U.S. Pat. No. 4,807,268 filed Feb. 26, 1986, for "Scanning Monochromator Crystal and Method of Formation" which itself is a continuation-in-part of U.S. Pat. application Ser. No. 549,366, now U.S. Pat. No. 4,599,741 filed Nov. 4, 1983, for "System for Local X-ray Excitation by Monochromatic X-rays".

The present invention relates generally to the art of radiation diffraction and, more particularly, to a scanning monochromator useful in diffracting and selectively monochromatizing radiation emanating from a point source.

It is often desirable to analyze radiation over a range of possible wavelengths to determine spectral content. Devices for doing so are called scanning monochromators. One circumstance in which scanning monochromators are useful is the analysis of fluorescence X-rays in a local X-ray excitation scheme of the type disclosed in the above-identified application, Ser. No. 549,366, the disclosure of which is hereby incorporated by reference.

Scanning monochromators analyze source radiation by moving a diffracting crystal and a suitable detector relative to the source location, typically along the circumference of a Rowland circle having a radius much greater than the length of the crystal. This causes the angle of incidence ($\theta$) on the crystal surface to vary continuously through a range over which radiation of different wavelengths is constructively reinforced by diffraction from planes of atoms in the crystal lattice. The resulting radiation is monochromatized at the wavelength that is constructively reinforced at any point in time, permitting the intensity of radiation at that wavelength to be detected with ease. Systems of this type are disclosed in Browning et al., U.S. Pat. No. 3,546,453 and Hara, U.S. Pat. No. 3,914,605, and the principles underlying them are described in "The Optical Principles of the Diffraction of X-rays", *The Crystalline State*, Vol II, R. W. James (1958).

Scanning monochromators of the prior art make use of flat or singly-curved crystals to provide a useful output over a range of Bragg angles. Doubly-curved diffraction crystals have been proposed in non-scanning devices to provide accurate focusing and good performance at certain specific Bragg angles, but the range of angles over which such crystals are useful has been so limited that they have not been considered suitable for scanning. A scanning monochromator must provide a reasonably consistent output over a wide range of Bragg angles.

Although prior scanning monochromators have high signal-to-background ratios in comparison to other instruments, the signal-to-background ratio available with flat or singly-curved crystals limits the sensitivity of such monochromators to low intensity signals. Therefore, in many applications it is desirable to provide a scanning monochromator with improved signal-to-background ratio and enhanced detection limits.

SUMMARY OF THE INVENTION

The present invention relates to a crystal arrangement for use in a scanning monochromator, which monochromator has a source location and an image location and is capable of producing relative movement between the source location, the image location and the crystal arrangement to vary the angle at which radiation emanating from the source location is diffracted. The crystal arrangement includes: a crystal positionable relative to a first reference plane containing the source and image locations, the crystal having concave planes of lattice points and a concave crystal surface which satisfy Johannson geometric conditions within the first reference plane for a Rowland circle of radius R; the planes of lattice points being substantially spherically curved with a radius of 2R within the first reference plane and a radius of substantially 2R within a second reference plane which is perpendicular to the first reference plane and bisects the Rowland circle; and the crystal surface being substantially toroidally curved with a radius of R within the first reference plane and a radius of substantially 2R within the second reference plane. In a preferred embodiment, the planes of lattice points are curved as a true sphere about a preselected point located at the circumference of the Rowland circle and opposite to the crystal surface, and the substantially toroidally curved surface is defined by rotating points on the Rowland circle about said preselected point in a direction perpendicular to the Rowland circle. In a further embodiment, the substantially spherical curvature of the planes of lattice points is only approximate and the crystal surface is curved as a toroid defined by rotating an arc of radius R about an axis which is tangential to the Rowland circle at the preselected point.

The invention also relates to a method of fabricating the doubly-curved crystal described above. The method involves preparing at least one crystal lamella having planes of lattice points and having an adjacent crystal surface which is curved cylindrically about a preselected axis; placing the lamella onto a convex mold curved to a preselected radius in the direction of cylindrical curvature and curved in a perpendicular direction to substantially twice that radius; covering the lamella with a continuous sheet of material able to withstand elevated temperatures; heating the mold, the lamella and the sheet to a temperature at which the sheet is flexible and at which the lamella can be deformed; and creating a partial vacuum beneath the sheet to draw it downwardly against the lamella and plastically deform the lamella to give the lamella a concave surface which matches the face of the mold.

The crystal of the present invention monochromatizes and substantially focuses a much higher proportion of the radiation impinging upon it from a point source than either the flat or the singly-curved crystals of the prior art. This is illustrated graphically in the drawings, wherein FIGS. 5A and 5B depict the diffracting surfaces of a doubly-curved crystal of the present invention and a singly-curved ("cylindrical") crystal of the prior art, respectively. The outlined areas represent portions of the two surfaces which are oriented such that radiation emanating from a point source within a central plane will impinge upon them at angles which deviate from a given Bragg angle by no more than a preselected amount. Of course, only the radiation which impinges on the crystal at substantially the Bragg angle, and which is focused on the image location, is useful in a scanning monochromator. Thus, a much larger solid angle of useful radiation is subtended by the crystal of the present invention, increasing the signal-tobackground ratio of the system. This difference is even more pronounced when the crystal of the present invention is compared to a flat crystal, for which only radiation impinging on a curved line passing through the center of the crystal reaches the detector.

Doubly-curved crystals of the type described herein are fabricated by plastically deforming singly-curved crystals having preselected cylindrical configurations of lattice planes and crystal surface. Deformation is accomplished by bending a crystal against a die or a mold in a process wherein bending forces are distributed as uniformly as possible over the crystal to avoid damage. Applicant uses a flexible sheet drawn downwardly by a partial vacuum to force the crystal over the mold.

BRIEF DESCRIPTION OF THE DRAWINGS

The above and other features of the present invention may be more fully understood from the following detailed description, taken together with the accompanying drawings, wherein similar reference characters refer to similar elements throughout and in which:

FIG. 2 is a diagrammatic representation of the monochromator of FIG. 1, showing its crystal and its radiation detector in two different positions relative to the source location;

FIG. 3B is a schematic cross-sectional view taken along the line 3B—3B of FIG. 3A;

FIG. 5A depicts the diffracting surface of the crystal of FIG. 3, with outlines showing portions over which radiation from a point source within the plane of the Rowland circle impinges at substantially the Bragg angle;

FIG. 5B shows similar outlines on the surface of a cylindrically-curved diffraction crystal which satisfies Johannson geometric conditions within the plane of the Rowland circle;

DESCRIPTION OF THE PREFERRED EMBODIMENTS

Figure 1:
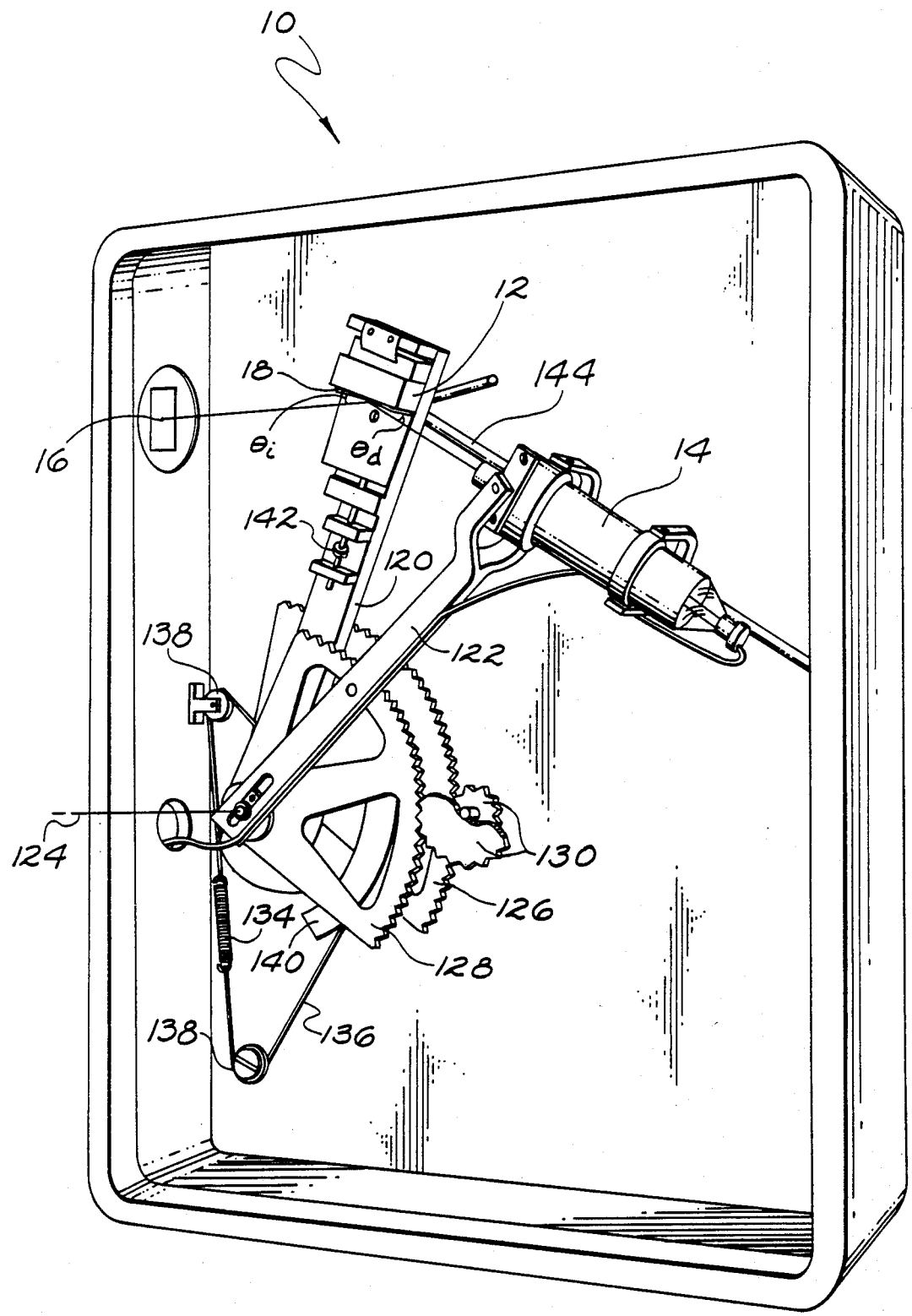
FIG. 1 is an isometric view of a typical scanning monochromator in which the crystal arrangement of the present invention is useful.

Referring to FIG. 1, a scanning monochrometer 10 constructed according to a preferred embodiment of the present invention contains a crystal arrangement 12 and a detector 14 mounted for movement relative to a source 16 of electromagnetic radiation to be analyzed. Movement of the crystal arrangement 12 and the detector 14 is controlled to vary the angle ($\theta_\iota$) at which radiation emanating from the source 16 impinges upon the crystal, while maintaining the detector in position to detect radiation diffracted at an aangle ($\theta_a$) equal to the angle of incidence. This "scanning" movement is illustrated in FIG. 2, wherein a crystal 18 and the detector 14 are shown in a first (full-line) condition in which source radiation is incident on the crystal at an angle ($\theta_{\iota 1}$), and a second (broken-line) condition in which source radiation is incident on the crystal at a smaller angle ($\theta_{\iota 2}$). The detector counts quanta of diffracted radiation as a function of the angle of incidence on the crystal.

For purposes of the present invention, the radiation emanating from the source location 16 can be any form of electromagnetic radiation having a wavelength ($\lambda$) no more than twice the lattice parameter (d) of the crystal. The radiation most often comprises X-rays, gamma rays or a neutron beam.

The crystal 18 may be formed of one or more crystal lamellae positioned side-by-side to provide the unique crystal geometry of the present invention. In either case, the crystal 18 satisfies Johannson geometric conditions within the plane of a Rowland circle of radius R which contains the source 16 and the detector 14, and has planes of crystal lattice points and a concave crystal surface which are curved appropriately in the direction perpendicular to the plane of the Rowland circle.

Figure 3A:
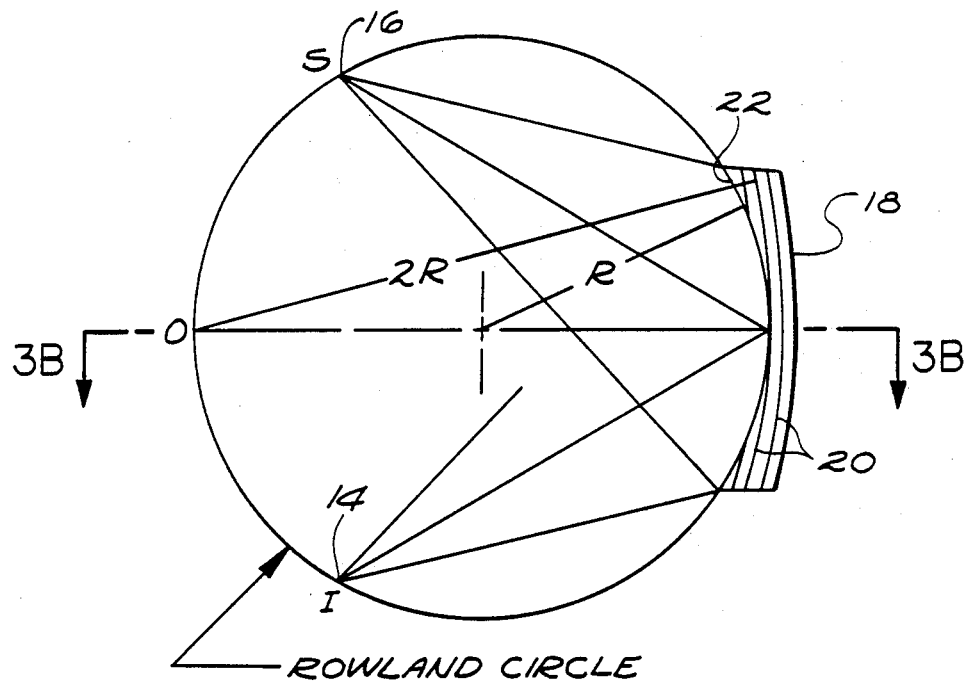
FIG. 3A illustrates a doubly-curved diffraction crystal useful in the monochromator of FIG. 1, which crystal is shown schematically within the plane of the Rowland circle.

The geometry of the crystal 18 in the plane of the Rowland circle is shown in FIG. 3A. The crystal 18 has convex planes of lattice points 20 curved to a radius of 2R about an origin O located on the circumference of the Rowland circle and opposite to the crystal, and has a convex surface 22 curved to a radius of R about the center of the Rowland circle. In accordance with Johannson conditions, radiation emanating from the source 16 encounters the planes 20 at a uniform angle over the surface 22 and are focused at an image location I corresponding to the detector 14 of FIGS. 1 and 2. All radiation emanating from the source S and subtended by the crystal 18 within the plane of the Rowland circle are focused onto the detector 14.

In a plane perpendicular to and bisecting the Rowland circle, the planes of lattice points 20 and the crystal surface 22 are curved to radii substantially equal to 2R. This profile is illustrated generally in FIG. 3B. Thus, the planes 20 are curved substantially spherically to a radius of substantially 2R and the surface 22 is curved substantially toroidally with a radius of R in the plane of the Rowland circle and a radius of substantially 2R in a plane perpendicular to the Rowland circle. In a preferred embodiment, the toroidal contour of the surface 22 is defined by rotating the circular profile of the surface in the plane of the Rowland circle about an axis which is tangential to the Rowland circle and contains the origin O.

As used herein, the term "substantially spherically curved" defines a shape of crystal planes in which the radii of curvature in two perpendicular directions can vary up to 20 percent from each other without defeating the utility of the crystal in a scanning monochromator. The planes of lattice points are preferably curves as a sphere with radii equal to precisely 2R (twice the radius of the Rowland circle) both in the plane of the Rowland circle and in a plane perpendicular to and bisecting the Rowland circle. However, acceptable results can be attained when the planes of lattice points are curved to a radius as small as 1.6R (20 percent less than 2R) in the plane perpendicular to the Rowland circle. Since the radius within the plane of the Rowland circle must equal 2R in order to satisfy Johannson conditions there, the resulting geometry is not curved as a "true sphere". Rather, it is toroidally curved with radii so nearly equal in perpendicular planes that it performs almost as well as the spherical case.

Likewise, the term "substantially toroidally curved" signifies a crystal surface which need not define a true torus. The surface can be defined by rotating points on the Rowland circle about a single point within planes perpendicular to the plane of the Rowland circle, rather than rotating the curve in the plane of the Rowland circle about a line to form a true torus. The radius within a plane perpendicular to the Rowland circle can vary up to 20 percent from the optimum value. In a preferred embodiment, the crystal surface is curved to a radius of R in the plane of the Rowland circle and to a radius of 2R in a plane perpendicular to and bisecting the Rowland circle. In accordance with the guidelines given above, the radius in the plane perpendicular to the Rowland circle may be as small as 1.6R without defeating the utility of the crystal for scanning.

Thus, the optimum geometry according to the teachings of the present invention is one in which the curvature of the planes of lattice points is as close as possible to that of a true sphere of radius 2R and the curvature of the crystal surface is as close as possible to that of a toroid of radius R in the plane of the Rowland circle and radius 2R perpendicular to the Rowland circle. Any deviation from this geometry by reducing the radii of curvature within planes perpendicular to the Rowland circle approaches the toroidal geometry disclosed in the above-referenced patent application, Ser. No. 549,366, in which Johannson geometric conditions are met in all planes containing source and image locations for a specific predefined wavelength of radiation. In such cases, the signal-to-background ratio is enhanced for radiation having wavelengths very close to the predefined wavelength, at the expense of performance over the broader spectrum. Of course, "tuning" of this type must be minimized if a crystal is to remain useful in scanning monochromators. The highly tuned nature of prior doubly-curved geometries is largely responsible for the longstanding belief that this type of doubly curved crystal is not useful in scanning monochromators.

The doubly-curved crystal 18 receives a large proportion of the radiation incident on it from the point source S at angles very close to the Bragg angle ($\theta_B$) at which radiation from the point source impinges upon the center of the crystal 18, and monochromatizes the radiation according to established diffraction principles. At the same time, it focuses the diffracted radiation onto the image location I as a short, curved line. This is substantiated analytically by calculating the deviation of the sine of the incidence angle ($\theta = \theta_B + \Delta\theta$) at any given point on the crystal surface from the sine of $\theta_B$, and comparing it to a similar deviation calculated for the case of a cylindrically bent crystal which satisfies Johannson conditions within the plane of the Rowland circle.

Calculation of the Deviation of Sin $(\theta + \Delta\theta)$ from Sin $\theta$

Figure 4:
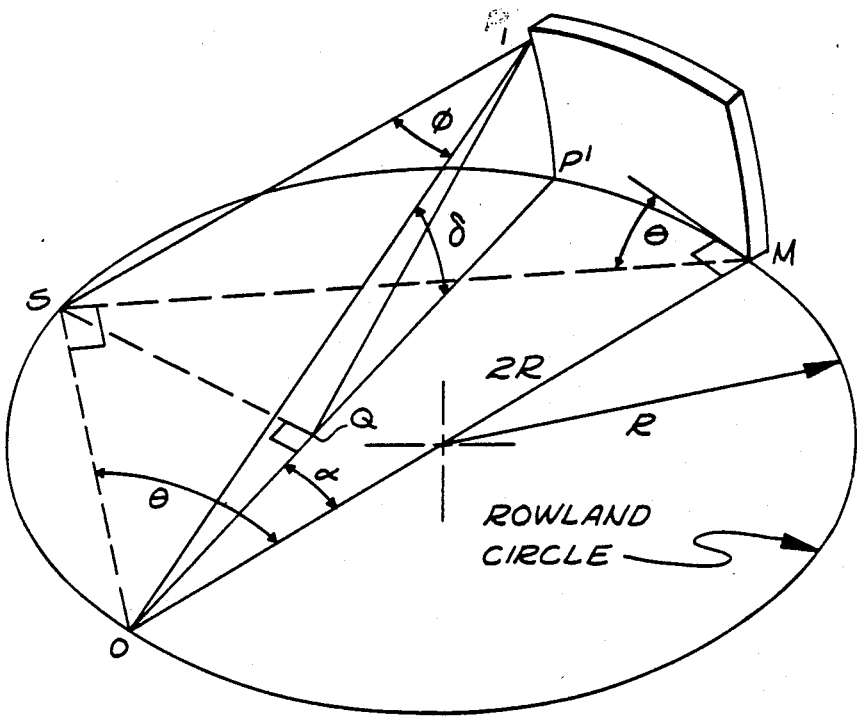
FIG. 4 is an isometric view of one quarter of the crystal of FIG. 3, showing the Rowland circle about which it is curved.

The geometry for this calculation is shown in FIG. 4, wherein: R is the radius of the Rowland circle (for simplicity, the radius R is taken to be unity); S is the position of the radiation source; O is the center of curvature of the planes of crystal lattice points; M is the midpoint of the crystal; $P_1$ is an arbitrary point on the crystal surface; $\theta$ is the angle of incidence of the rays from S to M on the crystal planes (this is the Bragg angle, $\theta_B$, for a symmetrical crystal); $\phi$ is the angle between the normal to the crystal planes and the ray from S to $P_1$; $\alpha$ is an angle in the plane of the focal circle; and $\delta$ is an angle perpendicular to the focal circle. The planes of crystal lattice points are assumed to be curved as a true sphere of radius 2R and the convex crystal surface is formed by rotating each point P' on the circumference of the Rowland circle individually about the point O through an angle $\delta$ perpendicular to the plane of the Rowland circle.

When the point $P_1$ coincides with M, $\cos \phi = \sin \theta$. We would like to find $\cos \phi$ as a function of $\theta$, $\alpha$, and $\delta$. The calculation proceeds as follows:

In the triangle OSM, $$\angle OSM = \pi/2 \text{ and} \qquad (1)$$
$$\angle SOM = \theta; \therefore OS = \cos \theta.$$

In the triangle SQO, $$\angle SQO = \pi/2 \text{ by construction,} \qquad (2)$$
$$OQ = \cos\theta \cos(\theta - \alpha)$$
$$SQ = \cos\theta \sin(\theta - \alpha). \qquad (3)$$

In the triangle OMP', $$\angle OP'M = \pi/2; \therefore OP' = \cos \alpha. \qquad (4)$$
$$OP_1 = \cos \alpha \text{ by construction.}$$

Using the law of cosines for the triangle OPQ, $$(P_1Q)^2 = (OP_1)^2 + (OQ)^2 - 2(OP_1)(OQ)\cos\delta \qquad (5)$$

From equations 1, 2 and 4, this becomes $$(P_1Q)^2 = \cos^2\alpha + \cos^2\theta\cos^2(\theta - \alpha) - \qquad (6)$$
$$2\cos\alpha\cos\theta\cos(\theta - \alpha)\cos\delta.$$

Using the Pythagorean theorem for triangle SPQ, $$(SP_1)^2 = (P_1Q)^2 + \cos^2\theta\sin^2(\theta - \alpha) \text{ and} \qquad (7)$$
$$(SP_1)^2 = \cos^2\alpha + \cos^2\theta -$$
$$2\cos\alpha\cos\theta\cos(\theta - \alpha)\cos\delta.$$

Using the law of cosines for triangle $SP_1O$, $$\cos^2\theta = \cos^2\alpha + (SP_1)^2 - 2(SP_1)\cos\alpha\cos\phi. \qquad (8)$$

From Equations 7 and 8 we obtain:

$$\cos\phi = \frac{[\cos\alpha - \cos\theta\cos(\theta - \alpha)\cos\delta]}{[\cos^2\alpha + \cos^2\theta - 2\cos\alpha\cos\theta\cos(\theta - \alpha)\cos\delta]^{\frac{1}{2}}}. \qquad (9)$$

If $\delta = 0$, this reduces to the Johansson case and it is found that $\cos\phi = \sin\theta$. Now, let $\cos\delta = (1 - \delta^2/2)$. Recognizing that $\cos\phi = \sin(\theta + \Delta\theta)$ Equation 9 becomes:

$$\sin(\theta + \Delta\theta) = \qquad (10)$$
$$\frac{\sin\theta[1 + (\cos^2\theta + \cos\theta\sin\theta\sin\alpha)(\delta^2/2A)]}{[1 + (2\cos^2\theta + 2\cos\theta\sin\theta\sin\alpha)(\delta^2/2B^2)]^{\frac{1}{2}}}.$$

Where $A = \cos\alpha - \cos^2\theta\cos\alpha - \cos\theta\sin\theta\sin\alpha$,
$A \simeq 1 - \alpha^2/2 - \cos^2\theta(1 - \alpha^2/2) - \alpha\cos\theta\sin\theta$;
and $B^2 = \cos^2\alpha + \cos^2\theta - 2\cos^2\alpha\cos^2\theta - 2\sin\alpha\cos\alpha\sin\theta\cos\theta$,
$B^2 \simeq 1 - \alpha^2 + \cos^2\theta - 2(1 - \alpha^2)\cos^2\theta - 2\alpha(1 - \alpha^2/2)\sin\theta\cos\theta$.

Since $\delta^2$ occurs in the second terms of the numerator and the denominator of Equation 10, we substitute for A and B, retaining only first order terms in the Taylor series expansion. We obtain:

$$\sin(\theta + \Delta\theta) \simeq \sin\theta\left[1 - \frac{\cos^3\theta}{\sin^3\theta}(\alpha\delta^2/2)\right]. \qquad (11)$$

INTERPRETATION OF RESULTS

There are five factors that determine the effective area of a curved crystal used in a scanning monochromator. These factors are: (a) the accuracy of curvature of the crystal planes; (b) the degree to which the crystal surface conforms to the ideal surface; (c) the degree to which radiation penetrates below the crystal surface before being diffracted; (d) the width of the rocking curve for the crystal; and (f) the deviation ($\Delta\theta$) of the angle of incidence from $\theta$ at the surface for various regions of the surface. In this discussion we are concerned only with the latter two of these considerations.

The foregoing derivation gives $\sin(\theta + \Delta\theta)$. This may be related to the deviation from the Bragg angle $\theta$ as follows:

$$\sin(\theta + \Delta\theta) = \sin\theta\cos\Delta\theta + \cos\theta\sin\Delta\theta.$$

For small $\Delta\theta$, $$\Delta\theta = (\cos\theta)^{-1}[\sin(\theta + \Delta\theta) - \sin\theta]. \qquad (12)$$

Using Equation 11, $$\Delta\theta = \frac{\cos^2\theta}{\sin^2\theta}(\alpha\delta^2/2)$$

For optimum signal-to-background ratio, the maximum value of $\Delta\theta$ should be less than or approximately equal to the width (w) of the rocking curve at half maximum. Typically, w has values ranging from $3\cdot10^{-5}$ to $5\cdot10^{-4}$ radians, depending on the type of crystal and its surface treatment. For crystals that are plastically deformed, as is often the case when small focal circle radii are used, w can be as small as $5\cdot10^{-4}$ radians if the starting material is a nearly perfect crystal and no polygonization occurs as a result of heat treatment.

For monochromators used in X-ray spectrochemical analysis, another factor to be considered is the natural width of the characteristic X-ray lines. For K lines with photon energies (E) of 1–10 keV, a typical value for the full width at half maximum ($\Delta E$) is $3\cdot10^{-4}\cdot E$. Using Bragg's law ($n\lambda = 2d\sin\theta$) and $\lambda = hc/E$, it is found that $$\Delta\theta = \frac{\sin\theta}{\cos\theta} \cdot \frac{\Delta E}{E}.$$

Because the intensity as a function of spectrometer position is the convolution of the intensity distribution of the emission line and the spectrometer transmission function, it can be seen that a value of $\Delta\theta$ of approximately $4\cdot10^{-4}$ radians should be close to the value necessary to optimize the signal-to-background ratio.

COMPARISON OF RESULTS WITH CYLINDRICAL JOHANNSON GEOMETRY

Plots of the locus of points on the surface of the crystal of the present invention for which $\Delta\theta$ is a constant are shown in FIG. 5A for a crystal which is 2 cm wide, 4 cm long and has a focal circle 10 cm in radius. The area included within these curves is the area for which $\Delta\theta$ is less than the given value. For comparison, the cylindrically curved Johansson case is shown in FIG. 5B. It can be seen that the area for a given $\Delta\theta$ is greater for the doubly-curved crystal than for the cylindrically curved Johansson crystal. It can also be seen that the geometric efficiency of the doubly-curved crystal could be further improved by truncating the corners of the rectangular crystal.

Figure 6:
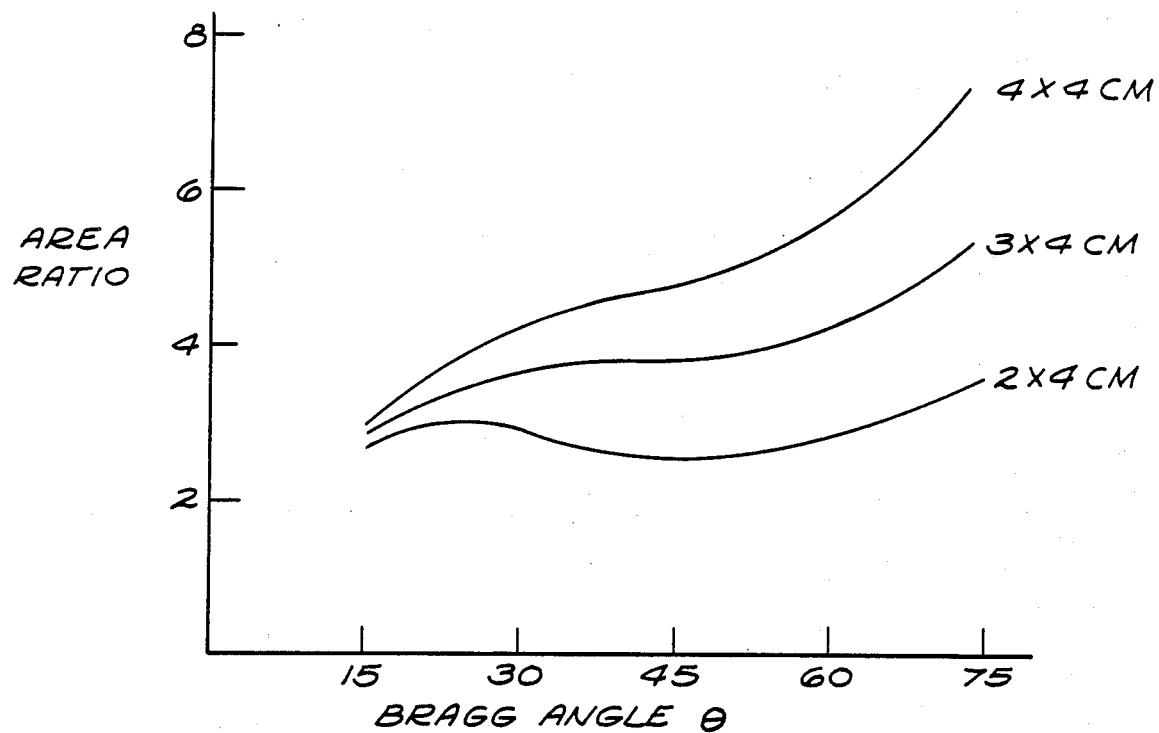
FIG. 6 is a graphical representation of the ratio between the "useful" area of the crystal of the present invention and that of a cylindrically-curved Johannson crystal, as a function of Bragg angle.

The ratio of the crystal area utilized in diffracting useful radiation in the geometry of the present invention to the area utilized in the cylindrically curved Johannson geometry is shown in FIG. 6 for $\Delta\theta = 4\cdot10^{-4}$ radians. The greatest improvement is obtained at large Bragg angles. This is expected since exact point-to-point focusing is obtained for $\theta = 90$ degrees (a physically unrealizable case).

The improvement in the performance of the disclosed doubly-curved crystal over the cylindrically curved Johannson crystal is even greater when the effects of penetration are taken into account. This is true because the planes of lattice points at the surface of the doubly-curved crystal come closer to satisfying the Bragg angle for points away from the center of the crystal than do the planes in the cylindrically curved Johannson case. Therefore, less penetration is required to reach a plane for which the Bragg condition is satisfied. For this reason, crystals having elements of high atomic number and large scattering factor may be preferred in the structure of the present invention over those having low atomic number. Such materials yield higher intensities of diffracted radiation, permitting even higher signal-to-background ratios. This is opposite to the consideration for monochromators using cylindrically curved Johannson crystals, in which the materials of low atomic number and low scattering factor are often required to achieve a suitable intensity. The contribution of diverging rays diffracted by planes below the surface is then quite important.

One material of high atomic number and large scattering factor which can be used in the crystal structure of the present invention is crystalline germanium. It is advantageous over the more commonly used alkali haide materials for the reasons described above. Silicon has an adequate scattering factor for these purposes and can be used because it has similar properties to germanium with respect to plastic deformation but is much less expensive.

TOROIDAL APPROXIMATION TO THE SPHERICAL CASE

Figure 7:
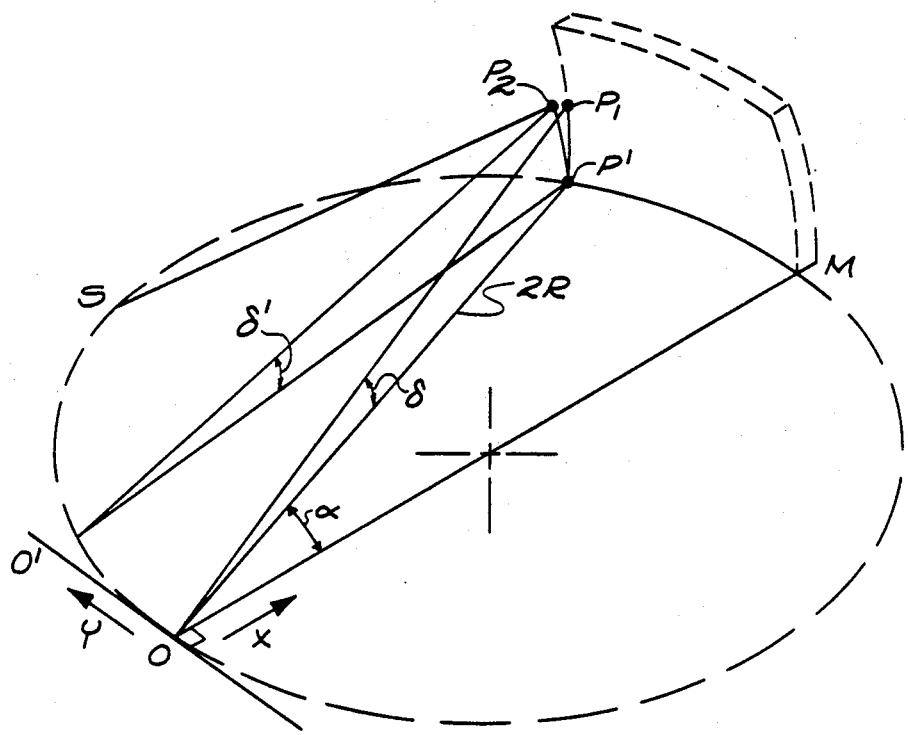
FIG. 7 is an isometric representation of the crystal portion of FIG. 4, illustrating two alternative curvatures of the crystal surface in the direction perpendicular to the Rowland circle.
Figure 8:
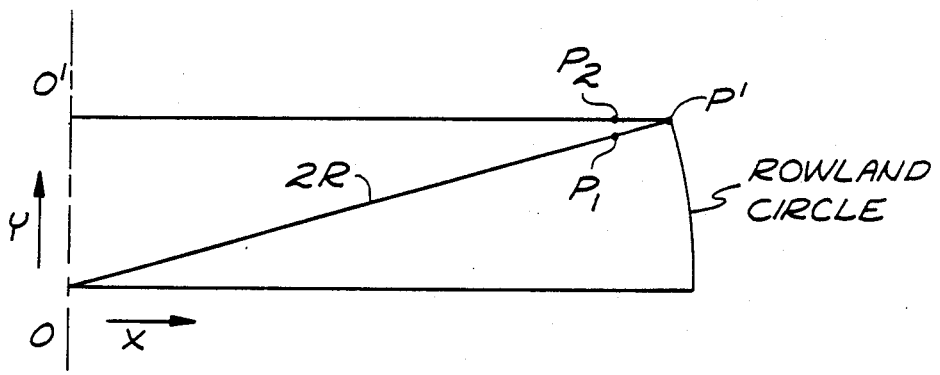
FIG. 8 is a top plan view of the representation of FIG. 7, showing the separation between equivalent points on the crystal surface for the alternative curvatures.
Figure 9:
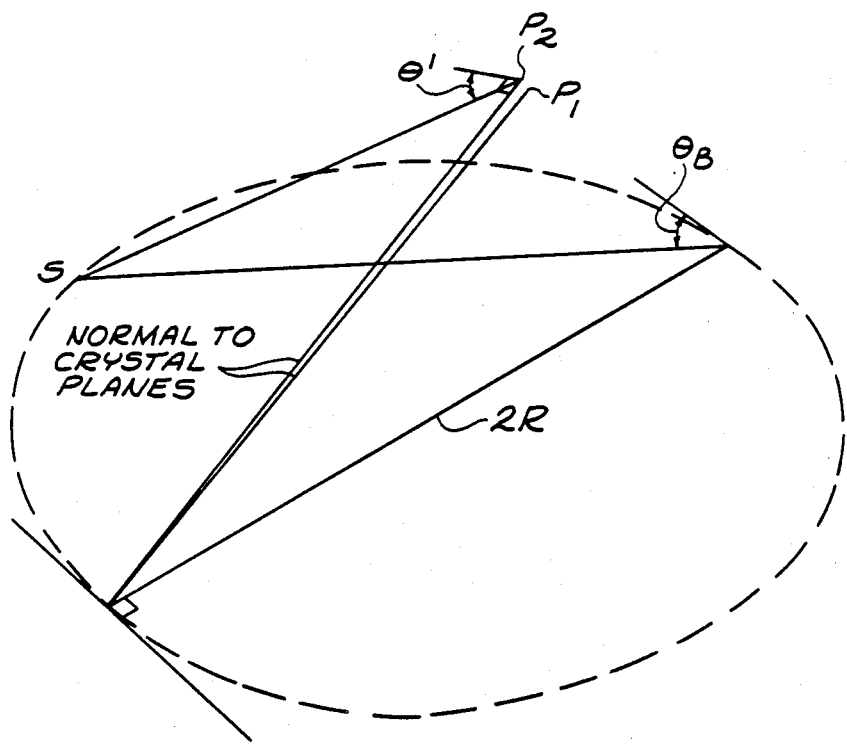
FIG. 9 is another isometric view showing the different angles of incidence encountered with the alternative curvatures of FIG. 7.

The calculations above were made for the case in which the line OP' is rotated about point 0 through an angle $\delta$. Alternatively, a truly toroidal crystal surface can be obtained by rotating the line O'P' about the axis 0'0 (FIG. 7) through a comparable angle $\delta'$. In the latter case, the position of final point ($P_2$) is not the same as the final position obtained above ($P_1$). This can be seen in FIG. 8, which is a plan view of the Rowland circle of FIG. 7. In FIG. 8, the point P' becomes $P_1$ in the optimum spherical case (Case A), and the point P' becomes $P_2$ in the more approximate toroidal case (Case B). As before, we take R, the radius of the Rowland circle, to be equal to 1. The rectilinear coordinates of $P_1$ and $P_2$ can then be expressed as follows:

| Coordinates of $P_1$ | Coordinates of $P_2$ |
| --- | --- |
| $P_{1X} = \cos^2 \alpha \cos \delta$ | $P_{2X} = \cos^2 \alpha \cos \delta'$ |
| $P_{1Y} = \cos \alpha \sin \alpha \cos \delta$ | $P_{2Y} = \cos \alpha \sin \alpha$ |
| $P_{1Z} = \cos \alpha \sin \delta$ | $P_{2Z} = \cos \alpha \cos \alpha \sin \delta'$ | noting that:
 $P_2$ is the same for both cases if $\sin \delta = \cos \alpha \sin \delta'$;
 $P_X$ does not change to terms of order $\alpha \delta^2$;
 $P_Y$ is smaller for case A by terms of order $\alpha \delta^2$, as can be seen by using a power series expansion;

$$\cos \alpha = 1 - \frac{\alpha^2}{2}, \sin \delta = \delta - \frac{\delta^2}{6}$$

$$P_{1Y} = \left(1 - \frac{\alpha^2}{2}\right)\left(\alpha - \frac{\alpha^3}{6}\right)\left(1 - \frac{\delta^2}{2}\right) + \ldots$$

$$P_{2Y} = \left(1 - \frac{\alpha^2}{2}\right)\left(\alpha - \frac{\alpha^3}{6}\right) + \ldots$$

Thus, for the toroidal surface also, only terms of order $\alpha \delta^2$ will be important in the expression:

$$\sin \theta' = \sin \theta [1 - K(\alpha \delta^2)].$$

This expression relates the angle ($\theta'$) at which radiation emanating from the source S impinges upon the crystal at the point $P_2$ of the truly toroidal surface to the comparable angle ($\theta_B$) at the center of the crystal. It is similar to an expression obtainable for the slightly different surface of the point $P_1$, except that the value of the coefficient K is slightly lower in the truly toroidal case.

Because it is simpler to manufacture a toroidal mold using conventional machine tools and because the results achieved with a toroidal surface are very close to those obtained by rotating points on the Rowland circle about a point, the truly toroidal surface geometry is preferred in some cases.

Figure 10:
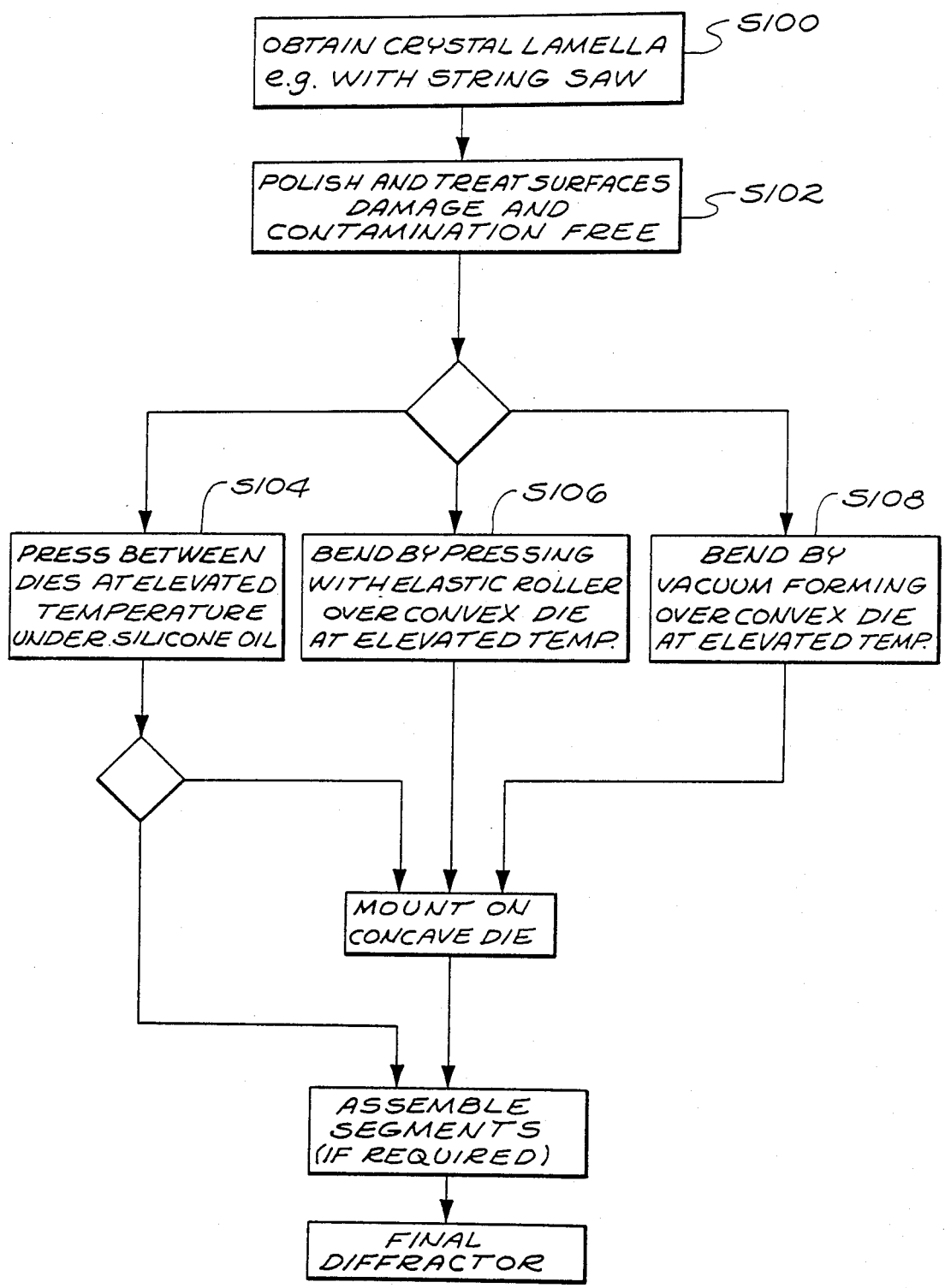
FIG. 10 is a flow chart illustrating the process of forming a diffraction crystal according to the method of the present invention.

Three methods of fabricating diffracting crystals for use in the practice of the present invention are outlined in FIG. 10. The first step, designated S100, is to obtain at least one crystal lamella 50 suitable for use in forming the diffracting crystal 18 of FIG. 3. The lamella is preferably cut from a single crystal of bulk material with a string or wire saw. The atomic planes of the bulk crystal are preferably flat and the lamella is cut to a radius equal to twice that of the Rowland circle for which it is intended. Alternatively, a flat crystal segment can be ground to the same radius, although this process is time consuming and wasteful of material.

Figures 11A, 11B, 11C:
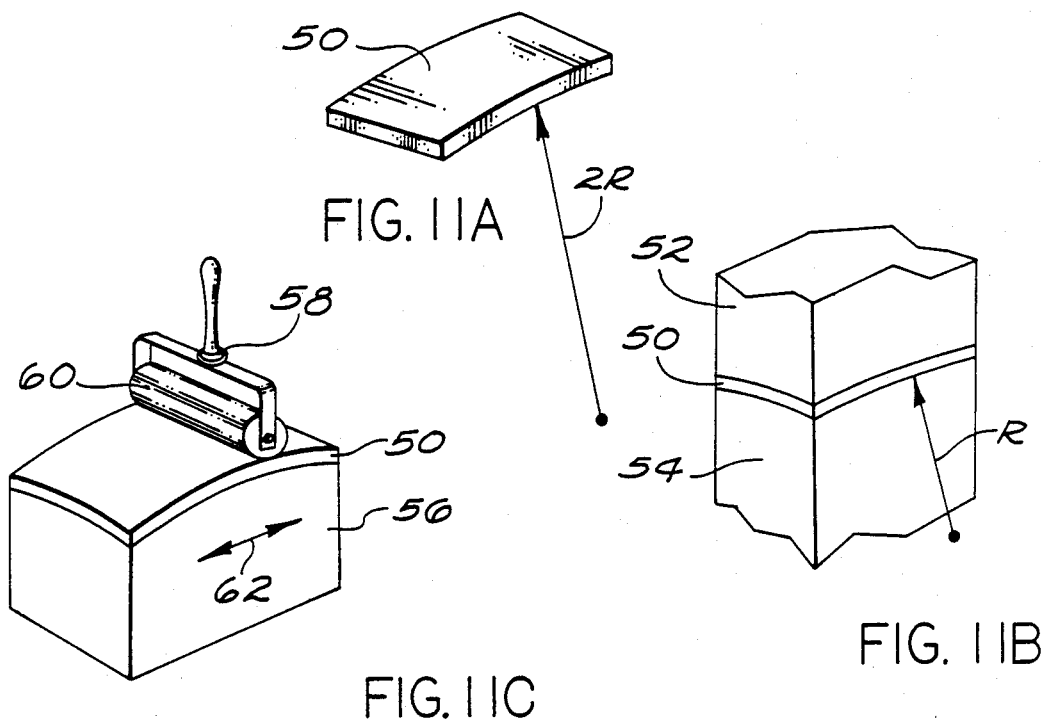
FIG. 11A is an isometric view of a cylindrically curved lamella from which the crystal arrangement of the present invention is formed.
FIG. 11B is an enlarged isometric representation of the lamella of FIG. 11A being shaped between a pair of dies.
FIG. 11C is an enlarged isometric representation of the lamella of FIG. 11A being shaped by rolling against a die.

The configuration of the lamella 50 after cutting is shown in FIG. 11A. The dimensions of the lamella must be small enough that the desired toroidal curvature can be achieved without exceeding the fracture limit of the material. Thus, it is necessary in some cases to form the crystal 18 of a plurality of distinct lamellae combined together to form a structure having the geometry disclosed herein. This can be done in the manner disclosed in the above-referenced patent application, Ser. No. 549,366. However, the crystals of the present invention are curved to significantly greater radii than those of the referenced application, reducing the strain involved in forming them. This enables the crystal to be made from fewer lamellae than are required in the device of the prior application, and often a single crystal lamella.

In an exemplary embodiment, the lamella 50 used to form the crystal is approximately 2 cm wide by 4 cm long, and is thin enough to be bent to the required radius. Thus, the maximum permissible thickness is lower for smaller radii so that the crystal can be more easily deformed. Taken generally, the maximum thickness is preferably $(1 \times 10^{-3})R$, where R is the radius of the Rowland circle. When the Rowland circle is 10 inches in radius, the thickness of the lamella may be as great as 10 mils.

The next step, designated S102, is to polish and treat the surfaces of the lamella so that they are damage- and contamination-free. This is particularly important for the surface to be placed in tension when the lamella is deformed. Cracks and surface imperfections are eliminated by polishing, and the surfaces may be treated by any of a variety of conventional techniques to aid in deformation. Alkali-halide crystals can be treated by soaking in a solvent or suitable etchant to trigger the Joffe effect. The crystals are then bathed in a suitable drying liquid to remove the solvent or etchant and prevent its evaporation on the crystal surface. In the case of NaCl, suitable solvent and drying liquids are water and alcohol, respectively. During the entire process, it is desirable to avoid exposing the crystal to ozone.

After the crystal surface has been treated and dried, the crystal is plastically deformed according to one of three processes, designated S104, S106 and S108, respectively, in FIG. 10. In step S104, illustrated schematically in FIG. 11B, the lamella 50 is pressed between upper and lower forming dies 52 and 54. This is preferably accomplished under a lubricant such as silicone oil. The lower die 54 has a convex upper surface (not shown) which conforms to the desired configuration of the crystal surface 22 (FIG. 30). Thus, the lower die has a radius of R in the plane of the eventual Rowland circle and a radius of substantially 2R in a plane which is perpendicular to and bisects the Rowland circle. The lower die may be made of silicone rubber to avoid damaging the crystal's surface.

In the alternative step S106, illustrated schematically in FIG. 11C, the lamella 50 is bent by pressing it downwardly over a lower convex die 56 using a forming roller 58. The roller has a rolling element 60 of suitable elastomeric material to yieldingly urge the fragile crystal lamella against the die. The process is preferably carried out at elevated temperatures, as with the other forming processes, to activate appropriate slip systems of the crystal. During the process, the roller 58 is passed back and forth over the crystal segment in a direction indicated at 62. A process of this type for fabricating cylindrically curved crystals is discussed in greater detail in Birks, *X-Ray Spectrochemical Analysis*, Appendix 2, pp. 127-131, Interscience Publishers, Inc., New York (1959), which is hereby incorporated by reference.

Figures 11D, 11E:
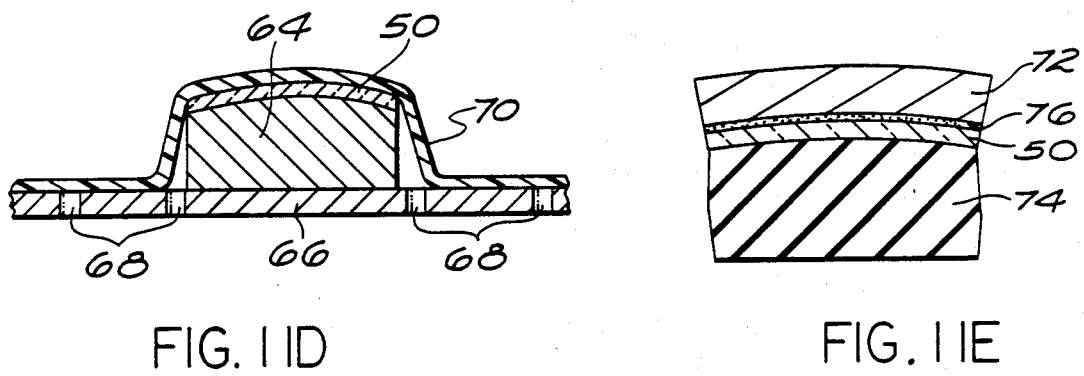
FIG. 11D is a vertical cross-sectional representation of the lamella of FIG. 11A being shaped by a vacuum-forming technique.
FIG. 11E is a vertical cross-sectional representation of the lamella of FIG. 11A being mounted to a concave backing member after shaping.

A further alternative step, S108, is illustrated in FIG. 11D. At present, it is the preferred method of crystal fabrication. In step S108, the crystal lamella 50 is bent by vacuum-forming it over a convex lower die 64 at elevated temperatures. The die 69 is positioned on a base plate 66 which has a plurality of holes 68 for evacuation of air around the die. When a continuous sheet 70 of elastomeric material is positioned above the lamella and the die, evacuation through the holes 68 causes the sheet to be forced downwardly by ambient air pressure against the lamella. The lamella is forced smoothly against the die until it conforms to the desired configuration. The sheet 70 can be made of any flexible material, such as buterate or silicone rubber, which is impermeable to air and possesses the tensile strength required to draw the crystal segment against the die. The attractiveness of this method lies primarily in the fact that the crystal is never contacted on its critical tensile side by a die or other rigid element applying a localized force. Rather, the force is distributed over the area of the crystal segment, minimizing the chance of breakage during the forming process.

After the lamella is formed by one of the steps S104, S106 or S108, it is preferably mounted for use on a concave mounting die 72 to form the crystal arrangement 12 of FIG. 1. This process is illustrated in FIG. 11E, wherein a crystal segment is engaged at the concave surface thereof by a convex die 79 which is preferably made of an elastomeric material such as silicon rubber or coated with such a material to avoid scratching the crystal segment. The segment is retained in position against the mounting die by a suitable adhesive 76.

Figure 12:
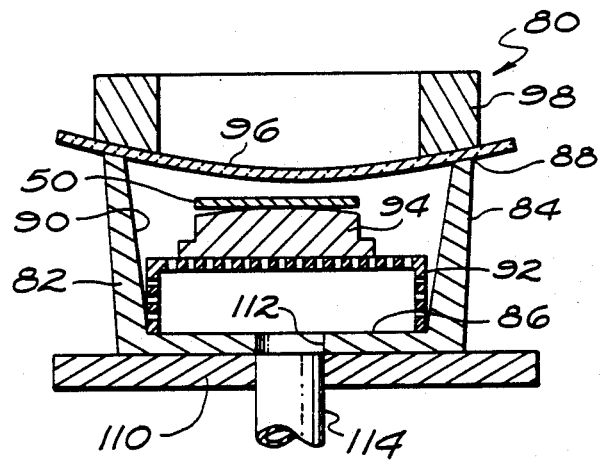
FIG. 12 is a vertical cross-sectional representation of an apparatus useful in shaping a lamella according to the vacuum-forming technique of FIG. 11D at elevated temperatures.

FIG. 12 illustrates a specific apparatus 80 for carrying out the vacuum-forming process of step S108 in a high temperature environment. The apparatus 80 includes a vessel 82 with side walls 84 extending from a bottom 86 to an open upper end 88. The walls 84 define a chamber 90 which contains a perforated table 92. An upwardly directed convex mold 94 is disposed on the table 92 to support the crystal lamella 50, and the open end 88 of the vessel is closed by a continuous sheet 96 and a weight 98.

The vessel 82 and the elements associated with it are made of materials able to withstand high temperatures, enabling them to be placed into an oven with the lamella 50 in place over the mold 94. The temperature of the oven is chosen so that the crystal lamella 50 and the continuous sheet 96 become flexible but are not damaged. After heat treatment, the apparatus 80 is removed from the oven and placed on a base 110 so that an opening 112 in the bottom of the vessel communicates with an upwardly directed fluid conduit 114. The chamber 90 is then at least partially evacuated through the conduit 114 and the opening 112. Air within the chamber passes freely through perforations of the table 92 to the vacuum hose 112, drawing the sheet 96 downwardly so that the lamella is effectively "pulled" over the mold 94. During this process, the lamella and the sheet 96 are maintained in a soft, flexible state by the heat of the vessel 82, the mold 94 and the weight 98. However, the mass of these elements should be kept as small as possible so that the lamella does not remain at elevated temperatures any longer than necessary after removal from the oven.

The temperature to which the apparatus 80 is heated depends upon the material chosen for the crystal lamella 50. Preferred temperature ranges are 600-700 degrees Celsius for germanium (Ge), 800-900 degrees Celsius for silicon (Si) and 300-400 degrees Celsius for certain ionic crystal materials. Suitable ionic crystal materials include alkali halides such as lithium fluoride (LiF), as well as ADP, PET and EDDT. The optimum temperature for treatment of lamellae made of a specific material is the range within which the material becomes soft enough to be deformed plastically without significant damage to its diffracting characteristics.

Because the temperature of heat treatment varies widely depending upon the crystal material used, the same material cannot be used for the continuous sheet 96 in all cases. The continuous sheet 96 must withstand the temperatures of heat treatment and be pliable enough at those temperaure to be drawn downwardly against the lamella. "Soft" glass is suitable for the range encountered with germanium, and heat-resistant glass of the type sold under the name "Pyrex" is preferred for the range encountered with silicon. In each case, the sheets are rigid at room temperature but become flexible at the temperatures of heat treatment. Silicone rubber can be used in the range of 300-400 degrees Celsius, as encountered in processing ionic crystal materials. The continuous sheet 96 is preferably between a fraction of a millimeter and approximately 2 millimeters thick.

When germanium and silicon are used as the diffracting crystal material, it may be necessary in some circumstances to make use of a suitable "parting medium" to prevent bonding of the sheet 96 to the lamella 50. Of course, the medium must be able to withstand the temperatures of heat treatment.

The fabrication process described above is designed to produce the necessary double curvature of the crystal material without disrupting the ability of the material to diffract radiation. In this process, it is desirable to produce a network of edge dislocations of the crystal lattice, rather than deforming the lattice in a series of "slip bands". After fabrication, the surface and atomic planes of the plastically deformed crystals can be investigated by X-ray topography, using a micro focus X-ray source.

The spatial resolution of a focused image obtained with the plastically deformed crystals of the invention depends upon the half-width of the rocking curve for the crystal and upon its primary and secondary extinction coefficients. Therefore, it may be desirable to resort to polygonization of the crystal to fine-tune its efficiency, either up or down. Polygonization, an increase in the size of mosaic blocks within a crystal lattice, is caused by final heat treatment. It may increase the primary extinction coefficient in one dimension by causing a coarsening of the structure near the surface. The effect is a trade-off, enhancing efficiency in some regions and reducing it in others. It is desirable to obtain an optimum size of mosaic blocks to maximize the integrated reflection coefficient and the primary extinction coefficient of the crystal, as described in R. W. James, "The Optical Principles of the Diffraction of X-Rays", *The Crystalline State*, Volume II, pp. 267–305, G. Bell & Sons, Ltd., 1958, which is hereby incorporated by reference. Heat treatment for polygonization would take the form of annealing at an elevated temperature. Execution of this step is well within the capabilities of one skilled in the art of crystal fabrication.

The rocking curve "half-width", which is actually the full width at half maximum, is the angular range over which the intensity of a diffracted beam drops to one half its maximum value as the angle of incidence varies from the Bragg angle. It is increased by imperfections in the surface and atomic planes of a crystal. An increase in the rocking curve half-width can have a beneficial effect on the efficiency of the crystal but causes a poorer-signal-to-background ratio and poorer focus. The rocking curve half-width can be increased by surface treatment, if desired. Specifically, such treatment can take the form of controlled grinding or abrading of the surface.

In use, the crystal 18 is mounted to the backing member 72 (FIG. 11E) and installed as the crystal arrangement 12 in a scanning monochromator such as that shown in FIG. 1. Referring to FIG. 1 in detail, the spectrometer has a first arm 120 and a second arm 122 mounted for rotation about an axis 124 as the spectrometer operates. The crystal arrangement 12 is carried near an outer end of the arm 120 and the detector 14 is carried at an outer end of the arm 122, both for movement with the arms relative to the stationary source location 16. Movement of the arms relative to each other and to the source location is controlled by sector gears 126 and 128 carried by the respective arms. The sector gears are interconnected by a pair of spur gears 130 which are mounted for common rotation about a second axis 132. The diameters of the sector gears 126 and 128 and the spur gears 130 are selected so that the detector 14 moves in the same direction as the crystal arrangement 12 and through twice the angle that the crystal arrangement moves. When the distance between the diffracting crystal surface and the axis 124 is equal to the radius of the Rowland circle of the crystal, the mechanism maintains the source location 16, the crystal arrangement 12 and the detector 14 at the surface of the Rowland circle in the classic diffraction geometry.

The arms 120 and 122 are biased by a spring 134 acting through a cable 136 to eliminate backlash of the gear train composed of the sector gears 126 and 128 and the spur gears 130. The cable 136 passes around a pair of pulleys 138 to engage arcuate guide members 140 associated with each of the arms.

Adjustment of the crystal arrangement 12 in a radial direction is permitted by an adjusting mechanism 142 on the arm 120. Similarly, alignment of the detector 14 relative to the crystal arrangement 12 is maintained by a guide rod 144 which is pivotally mounted to the arm 120 at a location near the crystal arrangement. The rod passes through a sleeve (not shown) carried by the detector 14 to keep the detector pointing toward the crystal.

The spectrometer 10 is operable to maintain the desired relationship between the source location 16, the crystal arrangement 12 and the detector 14 as relative movement occurs, varying the angle at which radiation emanating from the source location impinges upon the surface of the crystal 18. The detector 14 may be any form of proportional counter capable of measuring the intensity of incoming radiation at each angular orientation. The output of the counter thus provides information as to the spectral content of source radiation.

From the foregoing it can be seen that the unique geometry of the crystal arrangement 12, in the context of a scanning monochromator, provides a signal of higher intensity and better resolution over a broad spectrum of wavelengths than is obtainable using flat or singly-curved crystals. It thereby permits in-depth analysis of radiation sources which have heretofore been too weak for accurate measurement.

While certain specific embodiments of the present invention have been disclosed as typical, the invention is, of course, not limited to these particular forms, but rather is applicable broadly to all such variations as fall within the scope of the appended claims. For example, dimensional and geometric relationships described herein can be varied to some extent without interfering with the operation of the spectrometer. The bounds of such variation are set out generally herein. Features such as the number of crystal lamellae used to form the crystal structure can also be varied as needed, to produce the required geometry from a particular material. The number of lamellae depends on the characteristics of the material, the size of the crystal and the radius of the Rowland circle associated with the crystal. In addition, the scanning monochromator 10 may be of any suitable design and need not move the crystal in a circular manner. For instance, the crystal might be moved along a linear path to scan a range of wavelengths as encountered in commercially available electron probe microanalyzers.

I claim:

1. A crystal arrangement in combination with a scanning monochromator which has a point source and a mechanism for producing relative movement between the point source and the crystal arrangement to vary the angle at which radiation emanating from the point source impinges upon the crystal arrangement, the crystal arrangement comprising:

a crystal positioned with respect to a first reference plane containing the point source, the crystal having concave planes of lattice points and a concave crystal surface which satisfy Johannson geometric conditions within the first reference plane for a Rowland circle of radius R;

the planes of lattice points being substantially spherically curved with a radius of 2R within a second reference plane which is perpendicular to the first reference plane and bisects the Rowland circle; and the crystal surface being substantially toroidally curved with a radius of substantially 2R within the second reference plane.

2. The combination of claim 1 wherein:

the planes of lattice points are curved as a true sphere about a preselected point located on the circumference of the Rowland circle and opposite to the crystal structure; and the substantially toroidally curved crystal surface is defined by rotating points on the Rowland circle about said preselected point in a plane perpendicular to the Rowland circle.

3. The combination of claim 1 wherein:

the planes of lattice points are substantially spherically curved about a preselected point located on the circumference of the Rowland circle and opposite to the crystal surface; and the crystal surface has a curvature defined by rotating an arc of radius R about an axis which is tangential to the Rowland circle at said preselected point.

4. A scanning monochromator comprising:

a crystal positioned with respect to a first reference plane;

means for providing a point source of radiation incident on the crystal from a source location within the first reference plane;

means for responding to radiation diffracted by the crystal to an image location within the first reference plane;

means for producing relative movement between the point source, the means for responding to radiation and the crystal to vary the angle at which radiation emanating from the point source impinges upon the crystal and is diffracted to the means for responding to radiation;

the crystal having concave planes of lattice points and a concave crystal surface which satisfy Johannson geometric conditions for a Rowland circle of radius R within the first reference plane;

the planes of lattice points being substantially spherically curved with a radius of 2R within the first reference plane and a radius of substantially 2R within a second reference plane which is perpendicular to the first reference plane and bisects the Rowland circle; and the crystal surface being substantially toroidally curved with a radius of R within the first reference plane and a radius of substantially 2R within the second reference plane.

5. The scanning monochromator of claim 4 wherein:

the planes of lattice points are curved as a true sphere about a preselected point located on the circumference of the Rowland circle and opposite to the crystal surface; and the substantially toroidally curved crystal surface is defined by rotating points on the Rowland circle about said preselected point in a plane perpendicular to the Rowland circle.

6. The scanning monochromator of claim 4 wherein:

the planes of lattice points are substantially spherically curved about a preselected point located on the circumference of the Rowland circle and opposite to the crystal surface; and the crystal surface has a curvature defined by rotating an arc of radius R about an axis which is tangential to the Rowland circle at said preselected point.

7. A method of selectively monochromatizing radiation from a point source over a wide range of wavelengths, comprising:

placing a doubly-curved crystal in a position to diffract radiation from the point source at a first preselected Bragg angle and focus radiation having wavelengths monochromatized at said Bragg angle onto a detector at a separate image location;

causing relative movement between the point source, the detector and the doubly-curved crystal to diffract radiation from the point source at a plurality of other preselected Bragg angles and focus radiation having wavelengths monochromatized at said other Bragg angles onto the detector;

such that radiation emanating from the point source is scanned over a range of wavelengths.

8. The method of claim 7 wherein:

the doubly-curved crystal is positioned with respect to a first reference plane containing the point source and the detector, the crystal having concave planes of lattice points and a concave crystal surface which satisfy Johannson geometric conditions within the first reference plane for a Rowland circle of radius R;

the planes of lattice points being substantially spherically curves with a radius of 2R within the first reference plane and a radius of substantially 2R within a second reference plane which is perpendicular to the first reference plane and bisects the Rowland circle; and the crystal surface being substantially toroidally curved with a radius of R within the first reference plane and a radius of substantially 2R within the second reference plane.

9. The method of claim 8 wherein:

the planes of lattice points are curved as a true sphere about a preselected point located on the circumference of the Rowland circle and opposite to the crystal surface; and the substantially toroidally curved crystal surface is defined by rotating points on the Rowland circle about said preselected point in a plane perpendicular to the Rowland circle.

10. The method of claim 8 wherein:

the planes of lattice points are substantially spherically curved about a preselected point located on the circumference of the Rowland circle and opposite to the crystal surface; and the crystal surface has a curvature defined by rotating an arc of radius R about an axis tangential to the Rowland circle at said preselected point.

* * * * *

UNITED STATES PATENT AND TRADEMARK OFFICE
CERTIFICATE OF CORRECTION

PATENT NO. : 4,882,780
DATED : November 21, 1989
INVENTOR(S) : David B. Wittry

It is certified that error appears in the above-identified patent and that said Letters Patent is hereby corrected as shown below:

Col. 2, line 55, delete "and 5B" and substitute therefor --, 5C and 5E--;

Col. 2, lines 56 and 57, following "invention and" insert --Figures 5B, 5D and 5F depict--;

Col. 2, line 57, following "art" delete ", respectively";

Col. 3, line 39, delete "Figure 5A depicts" and substitute therefor --Figures 5A, 5C and 5E depict--;

Col. 3, line 39, delete "the", second occurrence, and substitute therefor --a--;

Col. 3, line 40, delete "of" and substitute therefor --constructed in accordance with--;

Col. 3, line 44, delete "Figure 5B shows" and substitute therefor --Figures 5B, 5D and 5F show--;

Col. 8, line 44, delete "the locus" and substitute therefor --various loci--;

UNITED STATES PATENT AND TRADEMARK OFFICE
CERTIFICATE OF CORRECTION

PATENT NO. : 4,882,780
DATED : November 21, 1989
INVENTOR(S) : David B. Wittry

Page 2 of 3

It is certified that error appears in the above-identified patent and that said Letters Patent is hereby corrected as shown below:

Col. 8, line 46, delete "Figure 5A" and substitute therefor --Figures 5A, 5C and 5E--;

Col. 8, line 48, delete "these curves" and substitute therefor --each curve--;

Col. 8, line 48, following "is", insert --therefore--;

Col. 8, line 49, delete the first incidence of "the" and substitute therefor --a--;

Col. 8, line 49, following "value.", insert -- The full line curves denote areas over which $\theta$ varies from the Bragg angle ($\theta_B$) by no more than $10^{-4}$ radians, the broken line curves denote areas over which $\theta$ varies by no more than $4 \times 10^{-4}$ radians, and the phantom line curves denote areas over which $\theta$ varies by no more than $1.4 \times 10^{-3}$ radians.--;

Col. 8, line 49, following "For comparison,", insert --the areas obtained in--;

UNITED STATES PATENT AND TRADEMARK OFFICE
CERTIFICATE OF CORRECTION

PATENT NO.   :   4,882,780
DATED        :   November 21, 1989
INVENTOR(S)  :   David B. Wittry It is certified that error appears in the above-identified patent and that said Letters Patent is hereby corrected as shown below:

Col. 8, line 50, delete "FIG"; and

Col. 8, line 51, delete "5B" and insert --Figures 5B, 5D and 5F--.

Signed and Sealed this

Twelfth Day of May, 1992

Attest:

DOUGLAS B. COMER

*Attesting Officer*   *Acting Commissioner of Patents and Trademarks*